United States Patent [19]

Hirao et al.

[11] 4,001,435

[45] Jan. 4, 1977

[54] PROCESS FOR PREPARING FOODS AND DRINKS

[75] Inventors: Mamoru Hirao; Yoshinori Sato, both of Okayama, Japan

[73] Assignee: Hayashibara Company, Okayama, Japan

[22] Filed: July 7, 1969

[21] Appl. No.: 839,689

[30] Foreign Application Priority Data

July 8, 1968   Japan ............................... 43-47650

[52] U.S. Cl. .................... 426/3; 426/103; 426/94; 426/310; 426/443; 426/567; 426/588; 426/575; 426/577; 426/580; 426/573; 426/592; 426/599; 426/629; 426/643; 426/658; 426/660; 426/590; 426/659; 195/31 R

[51] Int. Cl.² ........................................ A23G 3/30

[58] Field of Search ....................... 99/142; 127/20; 195/237, 31, 31 P; 426/3, 103, 94, 310, 443, 567, 588, 575, 577, 580, 573, 592, 599, 629, 643, 658, 660, 590, 659

[56] References Cited

UNITED STATES PATENTS

| | | | |
|---|---|---|---|
| 3,137,639 | 6/1964 | Hurst et al. | 195/31 |
| 3,565,765 | 2/1971 | Heady et al. | 195/31 |

FOREIGN PATENTS OR APPLICATIONS 1,144,950   3/1970   United Kingdom ................ 99/141

OTHER PUBLICATIONS

Kjolberg et al., 86 Journal of Biochemistry 258 1963 pp. 258–262.
Lee et al., 116 Archives of Biochemistry and Biophysics (1966) pp. 162–167.
Jacobs Chemistry and Technology of Food & Food Products Interscience Publishers Inc. New York 1951 pp. 67–70.

*Primary Examiner*—Raymond N. Jones
*Attorney, Agent, or Firm*—Browdy and Neimark

[57] ABSTRACT

A process for preparing foods and drinks sweetened and protected against coloration, Strecker's reaction, and moisture absorption, by the addition of high purity maltose, the maltose being produced by action of alpha-1,6-glucosidase and beta-amylase to enzymatically liquefied starch which consists essentially of amylopectin thereby producing straight-chain amylose and then subjecting the resulting amylose to the action of beta-amylase to obtain high purity maltose.

13 Claims, No Drawings

PROCESS FOR PREPARING FOODS AND DRINKS

This invention relates to a process for preparing foods and drinks sweetened and protected against coloration, Strecker's reaction, and moisture absorption, by the addition of high purity maltose substantially all of which is maltose.

Sweetening sources hitherto relied upon generally in the preparation of foods and drinks have been cane sugar, grape sugar, artificial sweetening agents, fruit sugar, honey, acid converted sirup, malt sirup, and even solid syrups in some cases. Of these sweetenings, cane sugar in wide use as the sweetest is known to be rather too pungent for harmony with the flavors of canned fruits and drinks, especially as diets for infants. In addition, relatively poor solubility of cane sugar has not only made it impossible to provide a highly concentrated liquid sugar but has often rendered it difficult to prepare and preserve many different types of foods and drinks because of the high tendency towards crystallization and separation of the sugar. Grape sugar has relatively mild sweetness, but it is less soluble at low temperature and readily precipitates the sugar crystals. A major shortcoming of grape sugar is the possibility of coloration by heat or in the presence of a nitrogen compound. Artificial sweetening agents are unable to afford body to foods and drinks. They lack nutritive values and fail to produce any palatable flavor when employed singly. Starch sirups take the form of viscid liquids and are difficult to handle as compared with other sweetenings which usually occur in crystalline powder form. Moreover, acid converted sirups do not suit the palate of all because of the inherent stimulative sweetness. Malt sirups have substantial sweetness and are dietectically desirable. However, difficulties involved in their purification, the possibility of coloration, and excessive viscosity have extremely limited their applications. Fruit sugar is not purified without difficulty and is usually prepared as a sirup in mixture with glucose. It is disadvantageous because of very poor stability against heat.

The present invention is directed to the elimination of the foregoing disadvantages of the conventional sweetners. It is thus the object of the invention to provide a process for preparing foods and drinks by the addition of high purity maltose consisting substantially entirely of maltose thereby imparting mild sweetness to the foods and drinks, protecting them against coloration by heat, avoiding Millard's and Strecker's reactions which otherwise can take place in the presence of a protein, amino acid or the like in the system, eliminating any possibility of coloration of the edibles or of generation of gas from canned foods, and, moreover, giving suitable viscosity and flavor-retaining property thereto.

The high purity maltose to be used in the present invention is of such purity that the maltose content is not less than 90% on the dry basis. Ordinary maltose sirup and maltose extract which have been available commercially are prepared by either saccharifying starch with malt amylase or directly saccharifying and extracting malt powder, and the maltose contents of such products are about 50% at most. Thus maltose of commerce always contains a large percentage of high molecular dextrin and occurs as a highly viscous non-crystalline sirup having much impure colorant proteins. These disadvantages all combine to make the ordinary maltose unsuitable for use as an sweetner to foodstuffs.

For the purpose of the invention the term "high purity maltose" means one prepared in the following way. One of various starches consisting essentially of amylopectin, e.g., waxy corn starch, corn starch, potato starch, sweet potato starch, or soluble starch, is liquefied, while maintaining the highest molecular weight possible, with or without the use of a liquefying enzyme. The starch thus liquefied is cooled rapidly to from 45° to 50° C., and, before the starch begins retrogradation, alpha-1,6-glucosidase and beta-amylase are added thereto so as to hydrolysis the alpha-1,6-glucoside bonds of the amylopectin and obtain amylose with straight-chain bonds. This amylose is then thoroughly decomposed by beta-amylase to maltose. In this manner high purity maltose consisting substantially entirely of maltose is obtained.

Because the alpha-1,6-glucoside bonds which hinder the hydrolysis with beta-amylase are broken off beforehand by the alpha-1,6-glucosidase, the maltose prepared by the present process can be completely hydrolysed by beta-amylase to form a high purity maltose preparation containing from 90 to 95% maltose. As an alternative, maltose can be obtained, regardless of the alpha-1,6-glucoside bonds, by the action of beta-amylase produced by bacterial polymixers (ATCC 8523, British Pat. No. 1,130,398).

Preparation of maltose in accordance with the present invention is illustrated by the following example. One hundred grams of corn starch was gelatinized and dispersed in 300 ml. of boiling water, and heated at 130° C. for 5 minutes. Next, it was cooled to 45° C. and adjusted to pH 6.0, and a pullulanase salting-out enzyme (*Aerobacter aerogenes*) was added at a rate of 20 units per gram of the starch. Several hours later, when the viscosity decreased, beta-amylase (ATCC 8523) was added at a rate of 150 units per gram of the starch. The mixture was saccharified at 45° C. for 48 hours, and then heated, filtered, concentrated, and purified in the usual manner by decoloration with active charcoal. The resultant solution, on concentration up to a water content of 15%, yielded colorless crystals. Analysis of the product showed a saccharide composition of 93.0% maltose, 1.5% glucose, 4.0% maltotriose, and 1.5% balance, on the dry basis. The product thus represented a high purity maltose preparation.

Experimental study of this maltose as a sweetner for foods and drinks has led to the following findings. First, regarding the sweetness, this maltose is not as strongly pungent as cane sugar but is mild in sweetness. It lacks the thickness of cane sugar and gives a refreshing after taste. Since it is available in the form of crystalline powder, unlike malt jelly, it can be used as a condiment or extender to be admixed in organic acids, colorants and flavors in preparing juice powders, soup powders, "miso" powders and other powdery foods. Also, its mild sweetness can be taken advantage of in preparing chocolate and other candies and sweets. It is also adapted for the preparation of bottled and canned juices. Further, it may be sprinkled over fresh fruits such as strawberries and water melons to add to their real flavors. Although the maltose is less sweet than cane sugar, it tastes like grape sugar and is an excellent sweetening source because the population favoring too sugary sweets is steadily decreasing.

Second, as for the stability, the maltose according to the invention is stabilized against heat because its content of unstable reducing groups is about one half that is glucose. When heated together with an organic nitrogen compound such as protein or amino acid, it remains inactive and discolors due to so-called Millard's reaction, nor is there generation of carbon dioxide by Strecker's reaction. With these features, the maltose is capable of playing an important role in the preparation of foods and drinks. Even when candies are to be made by mere heating and evaporation, the materials containing the maltose may be boiled up to a suitable water content or temperature without the danger of coloring. When boiled with chest nuts to prepare marron glaces, for example, this maltose avoids browning and gives lightly yellowish marrons of attractive luster. In canned fish and meat it prevents the gas generation due to Strecker's reaction and, for this reason, it can be safely used in the preparation of canned foods such as meat. With a good chemical stability, it also finds applications as an extender or vehicle for various medicines with great advantage.

Third, this maltose is characterized by the property of resisting crystallization. It is less crystallizable than cane sugar and glucose. Although it forms minute hydrated crystals, the presence of some oligosaccharides therein contained retards the crystallization velocity to a considerable degree. Since the oligosaccharide contents can be varied by controlling the degree of liquefaction and of the saccharification D.E., it follows that the crystallinity can be suitably controlled with the percentages of the oligosaccharides contained. In addition, when used in mixture with other saccharides, the crystallization of the latter can be restricted by this maltose in the manner above described. The maltose can therefore be mixed in sugary drops to add up to the flavors while, at the same time, avoiding separation of sugar crystals. It may be added as well to sweet jellies and pastes in order to give a gloss which stimulates the appetite while inhibiting the crystallization. When mixed in soft cream, cream sandwich, fondant, etc., the microcrystalline maltose provides a smooth texture, which combines with the mild sweetness to give the best results.

Fourth, this maltose is obtained as crystalline powder because of the high purity as compared with malt jelly. Its solution contains extremely small percentages of oligosaccharides and dextrins. The maltose itself has a viscosity nearly equivalent to that of cane sugar and is not so viscid as malt jelly is. As a sweetening agent for general purpose, it is more useful than ordinary sugar. Further, the inherent sweetness combines with the stability to enable the maltose to provide a plain and balanced body to fruits and synthesized alcoholic drinks.

Fifth, the maltose corresponds to a bimolecular polymer of glucose and therefore has the effect of lowering the freezing points of ice candies almost comparable to the effect of ordinary sugar, thus solving the problem of lowering the freezing point which usually occurs with other synthetic sweetenings. Similar conclusion has already been drawn in connection with osmotic pressure. For these reasons, the maltose gives a satisfactory result when used in ice cream and the like. Moreover, when added to canned fruits, it can restrict the shrinkage of the fruit meat and maintain maximum yields in terms of solid volume.

Lastly, it should be noted that the medicinal effect of maltose upon the bowels has long been known from the literature. Oral administration of maltose promotes the growth of lactic acid bacteria in the abdomen, which in turn maintains a suitable pH level inside and helps relieve constipation. This beneficial effect, when considered with the nutritive value and mild sweetness, make maltose a suitable sweetening additive to foodstuffs in general. Especially, it is most suited as a sweetening agent for the diets of constipated patients.

As described above, high purity maltose has most desirable properties as a sweetening agent for foodstuffs. The present invention will be more fully described hereunder in conjunction with some examples thereof.

EXAMPLE 1

Preparation of Orange Juice

| | |
|---|---|
| Concentrated (1/5) fruit juice | 2000 g. |
| Citric acid | 340 g. |
| 10% orange emulsion | 75 cc. |
| Flavoring | Some |
| Colorant | 5 g. |
| Maltose | 14000 g. |
| Water | to a total volume of 100l |

A solution of the above composition was instantaneously sterilized in the usual manner and was filled, while hot, in a bottle washed and sterilized beforehand, and then was stoppered and cooled. It was now a final product for sale. The mild sweetness of maltose, in good harmony with the sourness of orange, gives the product body and ensures even distribution of the flavor in the juice.

EXAMPLE 2

Preparation of Juice Powder

High purity maltose powder was dried to a water content of 4.5 to 5% and sieved. One hundred parts of this maltose powder was thoroughly mixed with 3 parts of citric acid, one part of tartaric acid, 1.5 parts of sodium cyclamate, 0.1 part each of saccharin and sodium glutamate, and 1.5 parts of a powdered flavoring agent. The mixture was sprayed with a suitable amount of a colorant solution, and was fully mixed up and then dried. The mixture upon sieving yielded a salable product. It was readily soluble in water, avoiding caking and color change, and underwent little deterioration because of a good flavor retaining property. Delicate harmony between the sweetness of maltose and the sourness and fragrance of the other ingredients more than offset the trace of unpalatable taste of the artificial sweetening agent.

EXAMPLE 3

Preparation of Sweetened Powdered Milk

First, to illustrate the preparation of whole powdered milk, fresh milk was purified by the usual method through a clarifier, and 2.5% of maltose powder on the basis of the milk was dissolved therein. Next, the milk was sterilized by heating with a plate heater at 75° C. for 20 seconds, and was concentrated under reduced pressure by a vacuum condenser. When concentrated to a 50% solid, it was sprayed from the nozzle of a spray drier, whereby a dry powdered product was obtained. The product was granulated with a water content of 0.7%, and was readily soluble in the water. The maltose, a nutrient, had a sweetness which was not so pungent as ordinary sugar but was mild enough, in good harmony with the natural flavor of milk, to best suit the palate of babies and little children. Also, when the solution was condensed to a concentration of 30 to 50% and bottled or canned in sterilized state, it could be used like conventional condensed milk for the infants and for the addition to coffee, cocoa and other drinks.

EXAMPLE 4

Preparation of Canned Fish

A stock for canned fish was prepared from 30 parts of maltose (purity 90%), 40 parts of soybean sauce, and 20 parts of water, all by weight. Together with 150 g. of boiled fish meat, 50 ml. of this stock was filled in a No. 6 can. With the cover placed on top, the can was deaerated in steam for 20 minutes. While hot, the can was sealed in vacuum by a vacuum machine with a pressure of 20 mmHg. It was heated under a load of 8 lbs. for 90 minutes, and then immediately it was cooled and the amount of carbondioxide gas generated was measured. The amount was one-fourth of the values attained with the use of grape sugar or cane sugar under the same treatment, and was equal to the value with cane sugar. This means that the use of maltose avoids the production of any defective canned foods with excessive generation of carbondioxide gas. The sweetness of the stock harmonized well with the taste of the fish meat and made the food palatable with a good body. The stock was free from the thickness of ordinary sugar, conferred a suitable luster on the meat, and had a suitable viscosity.

EXAMPLE 5

Preparation of Bottled Marron Glace

Chestnuts stripped of their astringent skins were immersed in water overnight, and then were boiled in water for 2 hours. With the addition of alum, the meat was stiffened and the tint fixed during the boiling. The marrons thus obtained were then placed in a 50% maltose solution, heated at 90° C., and allowed to stand overnight in order to permit sweetening of the marrons by permeation throughout. On the following day, the marrons only were packed in a bottle, a 65% maltose solution was poured in, and the bottle was sterilized with steam for 60 minutes, and was finally sealed.

The marrons so bottled were golden yellow in color, finely lustrous, and kept shape. The mild sweetness of maltose added delicately to the flavor of the marrons. Unlike the case with cane sugar, the maltose caused no deficiency of coloring and no need of coloring. Furthermore, there was no danger of browning of the meat as with grape sugar. Altogether, the results indicated that maltose is a most suitable sweetening agent for the preparation of sweetened juicy marrons.

EXAMPLE 6

Preparation of Sweet White-bean Jam and Jelly

"Tebo" beans were washed with water, with the addition of the same amount of water, boiled for "straightening." The astringent juicy solution was removed once, and the beans were boiled again with the same amount of water, this time with some amount of soda added to soften the skin. The beans were screened out of the water, cooled in cold water, and then skinned off. The bean meat thus exposed was boiled up with stirring, and was completely skinned off on a jamming machine. The resultant was filtered, squeezed, and purified with water several times. Toward the end of this purification, the bean jam was finished pure white with 0.1% hydrogen peroxide. One part of the white bean jam prepared in this way was mixed with one part of maltose with a purity of 90%. With the addition of a 1:50 pure agar solution, the mixture was slowly kneaded up by boiling to a water content of 25%. The product was a snow white "youkan" (sweetened bean jelly) having mild sweetness and firm texture.

When one part of the white bean jam prepared as above was mixed with from 0.5 to 1 part of maltose and the mixture was boiled to a suitable water content, the product possessed suitable sweetness and flavor for use in the preparation of high-class Japanese cakes. For example, "sakura-mochi" (a traditional Japanese bean paste rice-cake wrapped in a cherry leaf) prepared by adding from 10 to 20% of maltose to glutinous rice and steaming the mixture with the bean jam enclosed therein was characteristic of Japan's classical sweet, with a blend of gentle sweetness and cherry-like fragrance.

EXAMPLE 7

Preparation of Artificial "Sake"

Ten kiloliters of artificial "sake" with an alcoholic content of 15.5% was prepared by a mash bill as follows:

| | | |
|---|---|---|
| Alcohol (90%) | 1.5 | kl. |
| Maltose (purity 87%), water content 30% | 510.12 | kg. |
| Sodium glutamate | 1.1 | kg. |
| Succinic acid | 7.2 | kg. |
| Lactic acid (75%) | 1.40 | kg. |
| Potassium hydrogen phosphate | 0.610 | kg. |
| Calcium hydrogen phosphate | 0.610 | kg. |
| Sodium succinate | 1.20 | kg. |
| Sodium chloride | 1.11 | kg. |
| Alanine | 0.370 | kg. |
| Glycine | 0.296 | kg. |
| Fermented liquor for seasoning | 3.33 | kg. |

Mashing of the above mixture, followed by decantation filtration, maturing, and pasteurization in the usual manner, gave an artificial "sake" having a good flavor and body and which looked and tasted like the finest of beverage of the type as the sweetness and adequate viscosity of maltose added to the flavor of the seasoning liquor and made it distinct from the ordinary artificial "sake" using grape sugar, starch sirup, etc.

EXAMPLE 8

Preparation of Ice Cream

A solution of the following composition was fed to a freezer in the usual manner:

| | |
|---|---|
| Milk fat | 15 % |
| Skim milk powder | 11 % |
| Maltose (purity 90%) | 20 % |
| Stabilizer | 0.3 % |
| Artificial sweetening | Some amount |
| Flavoring and citric acid | Suitable amounts |
| Water | 53 % |

The product tasted adequately sweet and gave a refreshing after taste. Because of its relatively high freezing point, the product was stable against heat.

EXAMPLE 9

Preparation of Hard Candy

An 80% solution of maltose (purity 90%) was concentrated by a vacuum boiler to a water content of 1%. The concentrate was taken out onto a cooling plate, where it was mixed with suitable amounts of citric acid, flavoring, and colorant. The mixture was shaped on rolls at 80° C. and cooled by the usual method to obtain a hard candy. As compared with ordinary hard candy, the product was less hygroscopic, more lustrous, and milder in sweetness, in good harmony with sourness of the other ingredients. On the other hand, the maltose helped stabilize the edible colorant and flavoring in the composition, thus giving a favorable result in maintaining the candy quality. Moreover, this candy when taken regularly proved beneficial to the bowels. It also could be a non-calory refreshment for women. As for the crispness or shortness which is an essential attribute of good candy, the product was by far the superior to ordinary jellies and other sugary sweet meats.

EXAMPLE 10

Preparation of Canned "Mikan" Oranges

Each can was partly filled with a 38 Bx. solution of 95% maltose as the sirup.

"Mikan" oranges were led through a hot water bath and peeled. After air drying for 30 minutes, they were divided into the individual segments. Next, the meat was treated with a 1% hydrochloric acid solution at 30° C., washed with water for 15 minutes, treated with 0.8% caustic soda at 28° C. for 20 minutes, purified with a stream of fresh water for more than one hour, and then packed in the can.

Each can contained 235 g. of the orange meat and 80 g. of the sweetened solution. After the packing, the can was hermetically closed by a vacuum seamer and was heated for pasteurization. The opening test was made three times; on the following day, one month later, and three months later. Each time the test sample was compared with similarly treated canned fruit with cane sugar and grape sugar sirups. The results invariably showed that the canned fruit of the present example had a better luster with a less reduction of the solids yield than that with grape sugar. The sirup was always less oily than those of cane sugar and grape sugar. The canned fruit obtained in this way was sweet-scented with balanced sourness.

EXAMPLE 11

Preparation of Boiled Fish Paste

To the meat of shark a small proportion of "guchi" (Sciaena Schlegelii) was added, and the mixture was cleaned with running water and dehydrated in the usual manner. Next, it was minced by a mincer and roughly ground mechanically. With the addition of 2.5% sodium chloride, 3% sugar, and 10% maltose, the mixture was thoroughly ground. The finely ground flesh was placed on a rectangular plate of wood and allowed to stand at room temperature. It rested snagly on the base plate. On completion of the gelation, the resultant was baked in a roasting oven at 180° C. The "kamaboko" thus prepared was elastic and flavorous. Compared with the product using sugar as the only additive, the product had by far the greater spring and richer flavor.

EXAMPLE 12

Preparation of "Ama-natto" (Sweetened Red Beans)

For 100 parts of "kintoki azuki" (large red beans) conventionally boiled soft in water, 170 parts of maltose was used. The total amount of the maltose was dissolved in the same amount of water to form a dilute nectar or sirup. The boiled beans were kept immersed in this sirup for 24 hours and then taken out of the bath, drained, and the sirup was heated to 100° to 104° C. The beans were again immersed in the sirup and allowed to stand for 24 hours to permit impregnation of the beans with maltose. On the following day, the beans were raised and swished off from the sirup. The sirup was heated to 105° to 110° C., the beans were thrown in, and the temperature was elevated. When the sirup began boiling, the heating was discontinued, and the beans were left as they were until the sirup temperature dropped to 50° C. The beans were then taken out and swished off from the sirup onto a layer of maltose, little by little, so that the beans could be thoroughly coated with the maltose.

Unlike the ordinary "ama-natto" that is sweetened and coated with sugar, this product was gently sweet and would not absorb moisture like the sugary product in highly humid weather, with no melting of sugar crystals on the surface. While it is sometimes in practice in the confectionary industry to add a small amount of an acid to permit red beans to be boiled soft and in fine color, the sugary sirup may be partly inverted to mar the tint of the product or make the bean surface too mucous or moisture-absorptive. Maltose eliminates any such possibility. Where it is desired to draw a distinction between the sweetness inside of the red beans and that on the surface, the beans may be finished on the surface with cane sugar in the usual manner instead of the finishing with maltose.

EXAMPLE 13

Preparation of Boiled Beans as Side Dish

| | |
|---|---|
| Black soy beans | 10.0 kg. |
| Maltose | 7.5 kg. |
| Soy sauce | 2.0 l |

Black soy beans were washed with water beforehand and freed from impurities, and were then kept immersed in about five times by volume of water to absorb the water overnight. Next, the impregnated beans were boiled and softened. The beans were boiled, with the addition of one-third of the total amount of maltose to be used, for 15 minutes. They were then boiled with another one-third of the maltose for 10 minutes, and again with the rest of the maltose for another 10-minute period. At this point, soy sauce was added and the boiling was continued for 5 to 7 minutes. The boiled beans were filled and packed in a vinyl bag in vacuum. The product was not unpleasantly sweetened by the addition of maltose in a larger amount than sugar in ordinary products. It was delicious and had a suitable luster thanks to the high saccharide concentration. It showed no trace of decay or any other change in appearance for weeks after the preparation.

EXAMPLE 14

Preparation of Preservable Food Boiled Down in Soy

A wide variety of edible materials may be boiled down in soy sauce to prepare preservable foods. These foods treated using maltose can have longer life than sugar-treated ones because maltose is milder in sweetness than sugar and hence may be used in a larger amount in order to attain the same sweetness, thus, at the same time, contributing to the extension of the shelf life of the product. Furthermore, the use of maltose in place of sugar prevents coloration of the food. The sirup to be employed in such case should be preferably of enzyme-converted sirup rather than acid-converted one.

In preparing soy-boiled minced cuttlefish, a concoction of the following composition was used for every kilogram of minced cuttlefish:

| | |
|---|---|
| Enzyme-converted sirup | 1.00 kg. |
| Maltose | 1.30 kg. |
| Sodium chloride | 0.02 kg. |
| Water | 300 cc. |
| Agar | 2 g. |

First, agar was placed in an oven together with water and boiled and dissolved. Sirup, maltose and sodium chloride were added, and were dissolved away by boiling. Minced cuttlefish was thrown into the concoction thus produced. The mixture was quickly stirred with a stirrer so as to concentrate the concoction and coat the minced cuttlefish uniformly with the concentrate. Immediately after the boiling down, the food was spread on a cooling table and cooled as by a fan to obtain the final product.

When maltose and enzyme-converted sirup were used, there was no possibility of browning and therefore no need of carrying out the operation so quickly as with the combination of sugar and acid-converted sirup. Although the amount of maltose used was more than 30% greater than the usual proportion of sugar, the sweetness thereby attained was mild. The high concentration of maltose limited the flow of the liquid, thus giving a highly decay-resistant boiled food.

EXAMPLE 15

Preparation of Sweet Jellies

| (1) Pectin jelly | |
|---|---|
| Maltose | 1,500 g. |
| Enzyme-converted sirup | 1,500 g. |
| Pectin | 40 g. |
| Citric acid | 9 g. |
| Sodium citrate | 4.5 g. |
| Colorant | Suitable amount |
| Flavoring | Suitable amount |

Pectin jelly was prepared from the materials according to the above recipe. The final finishing temperature was decreased from the temperature with the sugar-acid-converted sirup combination by 2° to 3° C., i.e., to 103° to 104° C.

In preparing a pectin jelly, it is to be noted that usually the pectin will not jelly with however large proportion of acid unless the product contains at least 50% of sugar, and if the acid content is decreased, the pectin will need as much as 75% of sugar for the jellying purpose. Consequently, the ordinary sugar-based jellies are too sweet to meet the palate of all. The adoption of maltose instead gives a far milder sweetness to the product. Maltose can be heated with an acid without the production of inverted sugar or sweating of the product as is the case with sugar. It thus enhances the merchandise value of the product.

| (2) Agar jelly | |
|---|---|
| The following materials were used: | |
| Maltose | 3 kg. |
| Starch syrup | 3 kg. |
| Agar | 0.14 kg. |
| Flavoring | Suitable amount |
| Colorant | Suitable amount |

Agar was immersed in water overnight. Next, it was dissolved with heat in a steam jacketed oven equipped with a stirrer. Maltose and starch sirup were added, and the mixture was boiled down while care was taken to avoid any drop of the pH below 5. When the temperature reached about 106° C., the heating was stopped. While being cooled, the resultant, with the addition of the colorant and flavoring, was either poured into a mold or was cooled down and packed in a bag. After solidification, the molded product was cut off, dried, and packed.

The jelly thus prepared was as mellow and sweet as the pectin jelly.

EXAMPLE 16

Preparation of Wafers

| (1) Cream wafers | |
|---|---|
| Maltose (microcrystalline or fine powder | 2,000 g. |
| Shortening | 1,000 g. |
| Lecithin | 1 g. |
| Lemon oil | 1 cc. |
| Vanila oil | 1 cc. |

A cream of the above composition was heated at 40° to 45° C. and was sandwiched between wafers to form cream wafers.

The product cream was smoother than that based on sugar. With moderate sweetness and refined savor, it overcame the drawback, or excessive sugariness, of the sugar-based products.

2. Sugar Wafers

A 30% gelatin solution was thoroughly bubbled, and a maltose solution boiled down at 110° to 115° C. was added, and the mixture was agitated to a state like fondant. It was applied or sprayed on wafers. The product was mildly sweet and not too sugary.

EXAMPLE 17

Centers for Chocolate Balls (Cream Chocolate)

Maltose and starch sirup at the following ratio were mixed with stirring:

| | |
|---|---|
| Maltose (microcrystalline or fine powder) | 90 ~ 95% |
| Starch syrup | 10 ~ 5% |
| Water | Some amount |

Further, a small amount of water was added, while the mixture was being thoroughly agitated. With or without the application of some heat to fluidize it, flavoring and colorant were added. The mixture was packed in starch molds by means of a depositor and half solidify. The starch was then screened off, and centers for chocolate balls were obtained.

The product was smoother than ordinary sugar-containing ones. Its sweetness was not too strong but was moderate. While the use of grape sugar has been considered in the industry to avert the thick sweetness of sugar, grape sugar is disadvantageous because its solubility is highly dependent upon changes in temperature and, in addition, because it absorbs much hydrate water upon cooling, thus forming hard crystalline lumps which render subsequent processing difficult. Maltose has no such disadvantage; it provides a product satisfactory in both taste and quality.

EXAMPLE 18

Butter Cream

| | |
|---|---|
| Maltose | 950 g. |
| Starch sirup | 150 g. |
| Water | Suitable amount |
| Oil & fat (shortening) | 1,000 cc. |
| Flavoring & liquor | Suitable amount |

Maltose was dissolved in water by heating. With the incorporation of starch sirup, the mixture was boiled at about 105° C. down to a sirupy state, and cooled. Next, it was gradually poured into the shortening being stirred by a mixer. At the point where the mixture attained a smooth luster, the flavoring and liquor were introduced therein to obtain a final product.

The product was particularly smooth and pleasant to the palate. It was not too sweet and best suited for the preparation of decoration cakes.

EXAMPLE 19

Custard Cream 500 g. of corn starch, 900 g. of maltose, and 5 g. of sodium chloride were sieved and mixed well. 1400 g. of egg was added with stirring, and then 5,000 cc. of boiling milk ws added, little by little, with stirring. The mixture in a vessel was placed over a slow fire and the agitation was continued until the corn starch was completely gelatinized and the whole mixture became transparent. The fire was put off, and the resultant was cooled. With the addition of a flavoring as the final touch, a custard cream was obtained.

It was not thickly sweet but was extremely smooth and delicious.

EXAMPLE 20

Preparation of Chocolate

| | |
|---|---|
| Cacao liquor | 15 parts |
| Cacao butter | 19 parts |
| Powdered milk | 20 parts |
| Sugar | 46 parts |
| Lecithin | 0.6 part |
| Flavoring | Small amount |

Of the ingredients mentioned above, the sugar consisted of (1) powdered cane suger, (2) powdered cane suger and maltose at a mixing ratio of 1:1, or (3) maltose (95%-pure microcrystalline powder with a water content of 3.5%), and thus butter creams of three different compositions were prepared in the usual manner.

The three samples were compared throughout the refiner, quenching, tempering, molding and cooling stages, and were subjected to organoleptic tests to determine their sweetness, outward appearance and taste.

Refiner operations were invariably carried out smoothly without appreciable difference. Quenching was done all at 45° C., and tempering at 30° C. As for molding, the flow was smooth and workable, and the molded pieces were cooled at 17° C.

The product containing maltose according to the present invention was lustrous with a fine texture and was soft and tender. A storage test for a two-month period indicated only negligible moisture absorption by the present sample, and hence less sugar bloom and fat bloom than on the product using powdered cane sugar.

Sweetness of the sample was about 33 percent of the value of the cane sugar-base product. The products in which (2) a half of the cane sugar content was replaced by maltose or (3) only maltose was used as the sweetening, gave a greater degree of the bitterness associated with cacao than the cane sugar-based product did, and appeared to suit the modern palate. The limited moisture absorption and minute crystals of the maltose contained and small amounts of oligosaccharides present are considered contributory to the control and prevention of the growth of sugar cane crystals and also of the deposition of beta-crystals of fats, and therefore to the improvement of the texture.

It has heretofore been attempted at replacing thickly sweet cane sugar with grape sugar which is as mild as maltose in sweetness. However, anhydrous grape sugar and crystalline grape sugar are both inferior in processability because their solubility and moisture absorption increase with heat and neccessitate enhanced processing temperatures for refiner, quenching and other operations. Moreover, the products rapidly absorb moisture and tend to become moldy. These drawbacks have combined with a tendency for abrupt deglossing of the surface as by sugar bloom to discourage the adoption of grape sugar. Maltose is free from all such drawbacks and is as processable as refined sugar.

The results of property and organoleptic tests conducted with the product were as follows.

A. Moisture Absorption Test

1. Procedure

Samples of the maltose-containing products and control were placed in vessels wherein the humidity had been adjusted beforehand with sulfuric acid to 60, 70, 80 and 90 percent. The vessels were hermetically sealed with a glass plate each, kept still in a chamber thermostatically controlled at 30° C., and the moisture absorptions of the samples were compared.

2. Test samples

S100: Control, blended with sugar as the only sweetening

SM50: Composition in which 50% of sugar was replaced by maltose

M100: Composition in which all of sugar was replaced by maltose

3. Results

| | Moisture absorptions | | | | | |
|---|---|---|---|---|---|---|
| | RH 60% | | | RH 70% | | |
| | S100 | SM50 | M100 | S100 | SM50 | M100 |
| 1st day | 0.26% | 0.33% | 0.42% | 0.63% | 0.76% | 0.79% |
| 2nd day | 0.44 | 0.52 | 0.66 | 0.89 | 1.05 | 1.08 |
| 4th day | 0.59 | 0.68 | 0.78 | 1.04 | 1.25 | 1.38 |
| 8th day | 0.82 | 0.98 | 1.06 | 1.22 | 1.38 | 1.68 |
| | RH 80% | | | RH 90% | | |
| | S100 | SM500 | M100 | S100 | SM50 | M100 |
| 1st day | 1.55% | 2.39% | 1.52% | 2.88% | 3.82% | 2.27% |
| 2nd day | 2.29 | 2.97 | 2.12 | 5.56 | 6.68 | 3.77 |
| 4th day | 3.50 | 5.14 | 3.29 | 11.66 | 12.01 | 4.64 |
| 8th day | 6.49 | 9.22 | 3.96 | 16.08* | 16.99* | 7.57* |

*became moldy

B. Penetration Test

1. Procedure

After tempering, each test sample was molded and allowed to stand at 30° C. for 20 hours. Then, with a needle equipped with a 145 kg. weight, the penetration degree was determined.

The penetration degrees of the samples attained after five seconds of the needling at a room temperature of 20° C. and a relative humidity of 65% were as tabled below.

2. Results

| Sample No. | 1 | 2 | 3 | 4 | 5 | 6 | Average |
|---|---|---|---|---|---|---|---|
| S100 | 1.40 | 1.32 | 1.32 | 1.35 | 1.31 | 1.33 | 1.34 |
| SM50 | 1.35 | 1.40 | 1.36 | 1.32 | 1.34 | 1.37 | 1.36 |
| M100 | 1.36 | 1.37 | 1.35 | 1.40 | 1.39 | 1.33 | 1.37 |
| | | | | | (unit : cm) | | |

C. Droop Test for Chocolate Bars

1. Procedure

Test chocolate bars, 11.5 cm. long, were placed crosswise on a support beam, 10 cm. wide, and placed in a thermostat at 30° C. for different periods of 17, 96 and 108 hours. Then, the test bars were cooled to a room temperature of 20° C. and maintained at that temperature and at a relative humidity of 65% for 30 minutes before the degrees of droop were determined.

2. Results i. After standing for 17 hours:

| | A | B | C | Average |
|---|---|---|---|---|
| S100 | 3.00 | 3.35 | 3.25 | 3.20 |
| SM50 | 2.50 | 2.80 | 2.80 | 2.70 |
| M100 | 3.00 | 3.25 | 3.10 | 3.12 |
| | | | | (unit : mm) | ii. After standing for 96 hours:
| S100 | 11.5 mm ) | The test bars drooped |
| SM50 | 8.0 mm ) | progressively, but would |
| S100 | 8.0 mm ) | not break. | iii. After standing for 108 hours:
All drooped and gave way.

D. Fat Exudation Test

1. Procedure

Cubes of test samples, each measuring 1 cm³, were placed on filter paper and held altogether in a thermostat at 30° C. to determine the fat exudation through the paper.

2. Results

Exp. No. 1: A strip of filter paper carrying a test sample on one end was sandwiched between slide glasses and set in position. The samples of S100, SM50, and M100 tested in this way exhibited the same fat exudation or spread.

Exp. No. 2: When the above procedure was repeated except that a circular sheet of filter paper was used instead of the strip, the samples of S100, SM50, and M100 all exhibited the same pattern of spread.

E. Sugar Bloom Fat-bloom Test

1. Procedure a. Sugar bloom: On each test sample a dew point was artificially formed, and the sample was allowed to stand at a room temperature of 20° C. and a relative humidity of 65%.

b. Fat bloom: Each test sample was artificially heated (by direct exposure to the sun) to cause fat exudation on the surface, and the sample was then allowed to stand at 20° C. and RH 65%.

The sugar bloom occurred most noticeably on the S100 sample, followed by SM50 and M100 in the order mentioned. First, S100 turned white on the surface. M100 gave a slight indication of the bloom one month afterwards. As regards the fat bloom, there was no distinction observed among the samples.

F. Preference Test

1. Procedure

The three samples, i.e., A (S100), B (SM50) and C (M100), were tasted in a panel test and the evaluations were recorded in the order of preference. The examiners' opinions about the flavors, palatability and other qualities of the samples were also noted.

2. Results

The sample ratings by 27 examiners were as tabled below, according to the preference:

| | Number of examiners who rated the sample: | | | Total point |
|---|---|---|---|---|
| | 1st | 2nd | 3rd | |
| A | 4 | 5 | 18 | 68 |
| B | 6 | 16 | 5 | 53 |
| C | 17 | 6 | 4 | 41 |

No. of panels 27 )
No. of samples 3

The results obviously indicated significance in A, B, C, and also the superiority of C (M100) to the others.

G. Comparison of particles with commerical products

1. Procedure

A small amount of each sample was placed on a slide glass. With the addition of one drop of cedar oil, the sample was heated and dispersed and then observed through a microscope of 400 magnifications.

The results were as tabled below.

2. Results
L = maximum value; M = medium (10-sample mean) value; S = minimum value

|  |  | S100 | SM50 | M100 | "M" Co.'s chocolate black | "M" Co.'s milk chocolate deluxe | "F" Co.'s product |
|---|---|---|---|---|---|---|---|
| Sugar | L | 52.80 | 52.80 | 17.60 | 48.40 | 30.80 | 35.20 |
|  | M | 20.68 | 23.76 | 10.12 | 23.76 | 20.68 | 14.52 |
|  | S | 2.20 | 4.40 | 2.20 | 4.40 | 4.40 | 3.08 |
| Powdered milk | L | 48.40 | 57.20 | 44.00 | 39.60 | 44.00 | 154.00 |
|  | M | 19.80 | 23.76 | 24.20 | 14.96 | 20.24 | 17.16 |
|  | S | 4.40 | 4.40 | 4.40 | 4.40 | 8.80 | 4.40 |
| Cacao beans | L | 70.40 | 70.40 | 28.60 | 52.80 | 52.80 | 61.60 |
|  | M | 18.04 | 17.85 | 16.50 | 11.88 | 15.84 | 14.08 |
|  | S | 4.40 | 4.40 | 4.40 | 3.08 | 4.40 | 1.76 |

EXAMPLE 21

Preparation of Chewing Gum

|  | Control | I |
|---|---|---|
| Gum base | 120 g. | 120 g. |
| Acid-converted sirup (D.E. 45, water content 15%) | 60 g. | 60 g. |
| Powdered cane sugar | 320 g. | 160 g. |
| Maltose crystals (maltose 94%, water content 4%) | — | 160 g. |
| Citric acid | 1.5 g. | 1.5 g. |
| "San-ei" banana oil (Y2324) | 1.8 ml. | 1.8 ml. |
| "Takasago" banana oil (F8859) | 2.5 ml. | 2.5 ml. |
| Aluminum lake (Y4) | 0.3 g. | 0.3 g. |

The above materials were blended to prepare three different gums as follows:

| (1) | Control | (Sugar 100%) |
|---|---|---|
| (2) | Control:I = 1:1 | (Sugar:maltose = 3:1) |
| (3) | I | (Sugar:maltose = 1:1) |

Procedure for preparation: The gum base, sirup, and sweetening were mixed with heat and stirring on a mixer at a temperature of about 50° C. Next, the acid, flavoring and coloring were added with stirring. The mixture was taken out of the mixer, rolled flat, and molded.

The sweetness of the product became mild with the increase of the maltose proportion. The sample in which the sweetening comprised 50% maltose tasted most dainty. A satisfactory result was also obtained in respect of the keeping quality of the sweetness, an important atribute of the confection of this type. Hygroscopicity of the product was determined at different relative humidities of 50 and 70 percent. At RH 50%, all of the three samples tested showed negligible moisture absorption and were indistinct for that matter. The moisture absorptions at the end of a test period of 7 days at RH 70% was 0.56% for the control (1), 0.77% for (2), and 0.90% for (3), thus indicating only minor differences with no change in the appearance. The test further indicated that the moisture absorption sharply dropped to a constant value after the lapse of more than 7 days. Therefore, by using from 30 to 50% of maltose on the basis of powdered sugar, it is possible to moderate the sweetness without causing any appreciable change in the outward appearance as well as in the physical properties, and thus provide a chewing gum whose sweetness is left on the palate longer than that of ordinary sugary gums.

What is claimed is:

1. A process for preparing foods and drinks sweetened mildly, and protected against discoloration, Strecker's reaction, and moisture absorption, which comprises: adding $\alpha$-1,6-glucosidase and $\beta$-amylase, under such conditions and in a quantity sufficient to produce straight chain amylose, to enzymatically liquefied starch which consists essentially of amylopectin thereby producing straight-chain amylose; and subjecting the resulting amylose to the action of $\beta$-amylase and purifying and drying to obtain high purity maltose in crystalline powder form of 90– 95% maltose; and then adding said high purity crystalline maltose powder to foods and drinks as the essential added sweetener.

2. A method in accordance with claim 1 wherein said high purity crystalline maltose powder is added to said foods and drinks so as to constitute the major sweetener.

3. A method in accordance with claim 1 wherein said high purity crystalline maltose powder is added to said foods and drinks so as to constitute the sole sweetener.

4. A method in accordance with claim 1 for the preparation of canned food wherein said addition of said maltose is carried out by placing said food in a can and substantially filling said can with a water solution of said crystalline maltose as the major and essential sweetener, further comprising covering said can, deaerating and heating, vacuum sealing, heating and then cooling.

5. A method in accordance with claim 1 for the preparation of bottled marron glace comprising stripping chestnuts of their astringent skin, boiling said chestnuts for about 2 hours and adding alum thereto, placing the marrons thus obtained in a 50% solution of said maltose and heating to 90° C., permitting the marrons to stand overnight in said maltose solution to provide permeation of said maltose solution throughout said marrons, packing said marrons in a container, pouring a 65% solution of said maltose over said marrons in said container, sterilizing said container and sealing said container.

6. A method of making custard cream in accordance with claim 1 comprising adding said maltose in an amount of about 900 parts by weight to about 500 parts by weight of cornstarch and 5 parts by weight of sodium chloride, adding about 1400 parts by weight of egg with stirring, and then adding 5,000 parts by volume of boiling milk little by little with stirring, heating over a slow fire and containing mixing until the cornstarch is gelatinized and the mixture becomes transparent, and cooling.

7. A method in accordance with claim 1 for preparing chewing gum comprising adding said maltose in an amount of about 160 parts to about 120 parts of gum base and about 60 parts of acid converted syrup and about 160 parts of powdered cane sugar, heating the mixture to a temperature of about 50° C. with stirring, adding about 1.5 parts of citric acid and flavoring, and then molding.

8. A process in accordance with claim 3 wherein the food is sweet-white-bean jam and jelly which is produced by boiling beans, removing the skins from said beans, jamming the skinned beans, filtering, squeezing and purifying the jammed beans with water, leaching the filtered, squeezed and purified beans, and then carrying out said step of adding said high purity crystalline maltose powder to said bean jam in the amount of 1 part of white bean jam per 1 part of said maltose; adding 1:50 of pure agar solution; kneading the mixture and boiling to a water content of 25%.

9. A method in accordance with claim 2 for the preparation of boiled fish paste comprising mincing and grinding dehydrated fish meat; adding about 2.5% sodium chloride, about 3% sugar, and about 10% of said high purity maltose and thoroughly grinding the mixture; permitting the mixture to jelly; baking at about 180° C.

10. A method in accordance with claim 3 wherein the food is sweetened beans which are produced by mixing 100 parts of boiled soft beans with 170 parts of said maltose dissolved in water to form a dilute syrup; maintaining said boiled beans in said syrup for 24 hours; removing said beans and draining same; heating said syrup to about 100° C.; reimmersing said beans in said heated syrup and maintaining said beans in said syrup for about 24 hours; preheating said syrup to about 105° C. and adding said beans; heating the mixture until the syrup begins to boil and then discontinuing heating; maintaining said beans in said heated syrup until the temperature drops to about 50° C.; removing said beans from said syrup and dusting said beans with a quantity of said dry maltose.

11. A process for the preparation of preserved food boiled in soy in accordance with claim 2 comprising providing a mixed syrup of about 1.3 parts of said maltose, about 1 part of enzyme-converted syrup and about 0.3 parts of water with a small amount of agar; mixing said mixed syrup with about 1 part of minced cuttlefish; quickly stirring while heating so as to concentrate the concoction and coat the minced cuttlefish uniformly with the concentrate; and cooling.

12. A method in accordance with claim 3 wherein the food is cream wafers which are produced by mixing 2000 parts of said powdered maltose with 1,000 parts of shortening, 1 part of lecithin, 1 part of lemon oil and 1 part of vanilla oil; heating said mixture to about 40° – 45° C.; and sandwiching said mixture between wafers.

13. A method in accordance with claim 3 wherein the food is sugar wafers produced by thoroughly bubbling a 30% gelatin solution; preparing a maltose solution from said maltose powder and boiling down said maltose solution at 110° – 115° C.; adding said maltose solution to said bubbled gelatin solution; agitating said mixture; and applying said agitated mixture to wafers.

* * * * *